United States Patent
Gill et al.

(10) Patent No.: US 7,908,004 B1
(45) Date of Patent: Mar. 15, 2011

(54) CONSIDERING CARDIAC ISCHEMIA IN ELECTRODE SELECTION

(75) Inventors: Jong Gill, Valencia, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 440 days.

(21) Appl. No.: 11/847,878

(22) Filed: Aug. 30, 2007

(51) Int. Cl.
*A61N 1/00* (2006.01)

(52) U.S. Cl. .......................................................... 607/17

(58) Field of Classification Search ........................ None
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,058,092 A * | 10/1991 | Miyasaka | 369/44.27 |
| 5,466,254 A | 11/1995 | Helland | |
| 5,476,483 A | 12/1995 | Bornzin et al. | |
| 6,314,323 B1 | 11/2001 | Ekwall | |
| 6,377,852 B1 | 4/2002 | Bornzin et al. | |
| 6,381,493 B1 * | 4/2002 | Stadler et al. | 607/9 |
| 6,512,952 B2 | 1/2003 | Stahmann et al. | |
| 6,574,492 B1 * | 6/2003 | Ben-Haim et al. | 600/374 |
| 6,604,000 B2 | 8/2003 | Lu | |
| 6,615,089 B1 * | 9/2003 | Russie et al. | 700/21 |
| 6,628,988 B2 | 9/2003 | Kramer et al. | |
| 6,643,546 B2 | 11/2003 | Mathis et al. | |
| 6,725,085 B2 * | 4/2004 | Schwartzman et al. | 600/509 |
| 7,010,347 B2 * | 3/2006 | Schecter | 607/17 |
| 7,415,307 B2 * | 8/2008 | Sharma et al. | 607/17 |
| 7,450,988 B2 * | 11/2008 | Ross et al. | 607/9 |
| 7,509,170 B2 * | 3/2009 | Zhang et al. | 607/28 |
| 7,668,594 B2 * | 2/2010 | Brockway et al. | 607/9 |
| 7,684,863 B2 * | 3/2010 | Parikh et al. | 607/28 |
| 7,706,866 B2 * | 4/2010 | Zhang et al. | 600/512 |
| 2003/0055345 A1 | 3/2003 | Eigler et al. | |

OTHER PUBLICATIONS

Hofmann, Thomas et al., "Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function," J Am Coll Cardiol 1995;26:239-49.

Shioi, Tetsuo, et al., "Rapamycin Attenuates Load-Induced Cardiac Hypertrophy in Mice", Circulation. 2003;107:1664-1670.

Tsukada, Kosuke et al., "Development of catheter-type optical oxygen sensor and applications to bioinstrumentation," Biosensors and Bioelectronics 18 (2003) 1439-1445.

* cited by examiner

*Primary Examiner* — Mark W Bockelman
*Assistant Examiner* — Elizabeth K So

(57) ABSTRACT

Exemplary systems, devices, and methods for considering cardiac ischemia in electrode selection are described. One method determines whether an electrode of a multiple-electrode lead is proximate a region of cardiac ischemia or infarct. The method also paces through a different electrode of the multiple-electrode lead in an instance where the electrode is determined to be proximate the region.

12 Claims, 8 Drawing Sheets

CONSIDERING CARDIAC ISCHEMIA IN ELECTRODE SELECTION

FIELD OF THE INVENTION

The subject matter presented herein generally relates to implantable medical devices employed in cardiac settings and more specifically to considering cardiac ischemia in electrode selection.

BACKGROUND

Myocardial ischemia results from insufficient blood flow to the heart muscle. Ischemia may occur chronically such as due to coronary artery disease or acutely due to sudden increased demand, embolism or vasospasm. Ischemia can lead to angina and eventually to myocardial infarction—permanent damage to the heart muscle. Moreover, both ischemia and infarction can trigger fatal arrhythmias.

Many patients who are equipped with implantable medical devices (IMDs) such as cardiac pacing devices experience ischemia. In these patients the ischemia can affect the efficacy of any stimulation therapy supplied by the IMD to the cardiac tissue.

SUMMARY

Exemplary systems, devices, and methods for considering cardiac ischemia in electrode selection are described. One method determines whether an electrode of a multiple-electrode lead is proximate a region of cardiac ischemia or infarct. The method also paces through a different electrode of the multiple-electrode lead in an instance where the electrode is determined to be proximate the region.

One exemplary device includes an ischemia detection module for detecting cardiac ischemia or infarct in a region of cardiac tissue proximate a multiple-electrode lead. The device also includes an electrode selection module for selecting an electrode from the multiple-electrode lead that is relatively less proximate the region than another electrode of the multiple-electrode lead.

In general, the various techniques, methods, devices, systems, etc., described herein, and equivalents thereof, are optionally suitable for considering cardiac ischemia in electrode selection.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements wherever feasible.

DETAILED DESCRIPTION

Overview

Various exemplary techniques, methods, devices, systems, etc., described herein pertain to considering cardiac ischemia in electrode selection. Cardiac ischemia can decrease an effectiveness of a stimulation therapy applied to the heart. For instance, a pacing therapy that paces through cardiac tissue that is affected by the ischemia may produce a diminished response or may even aggravate the ischemia. The described implementations can detect cardiac ischemia and consider the ischemia in electrode selection for subsequent stimulation therapy such as pacing therapy. For example, some implementations can identify electrodes affected by the ischemia (i.e., positioned proximate the affected cardiac tissue). A region of affected cardiac tissue can be determined by correlating a position in the heart of the electrode(s) that detected the ischemia. These implementations can then select electrodes for pacing that lie outside the affected region.

Exemplary IMDs

Figure 1:
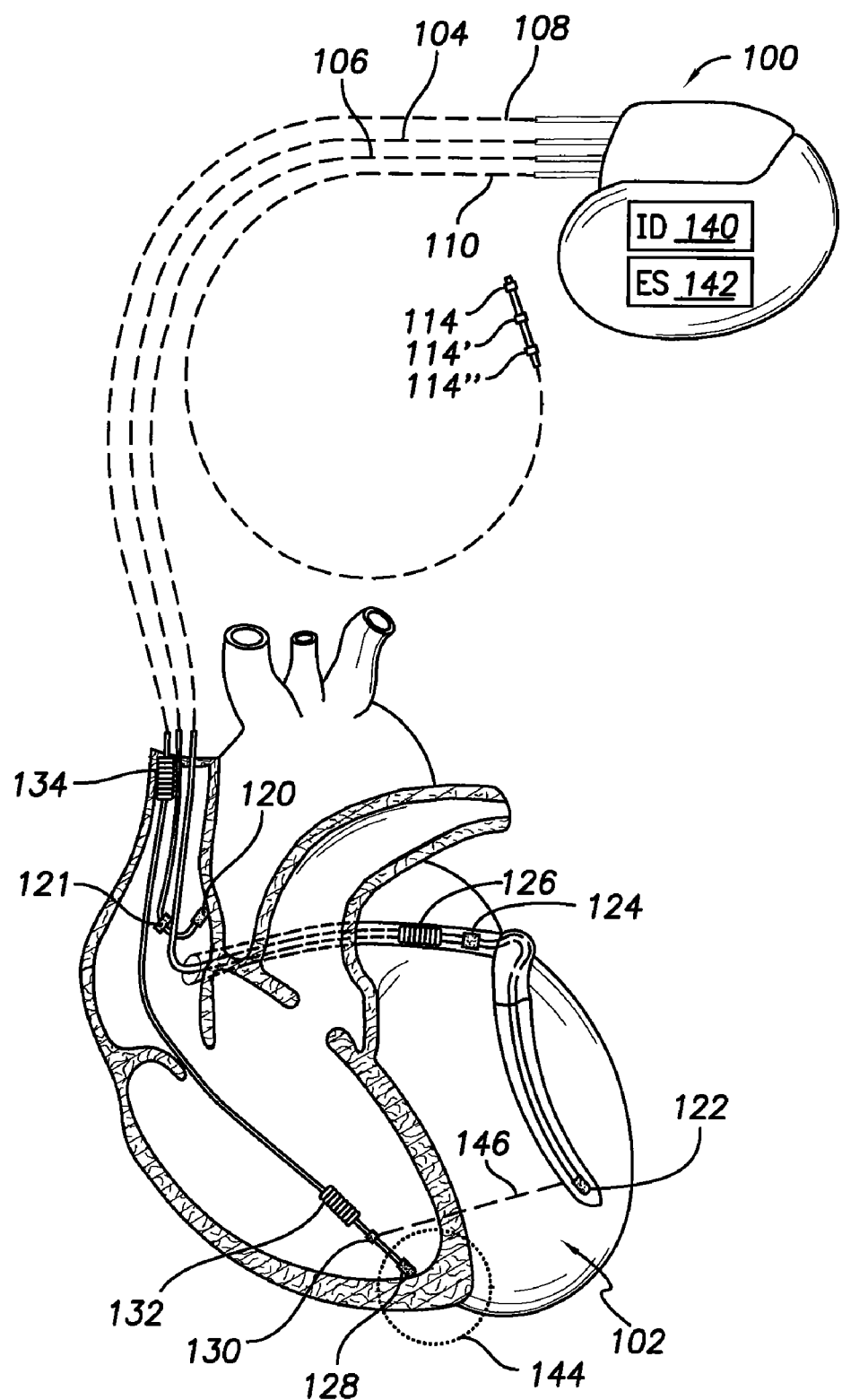
FIG. 1 is a simplified diagram illustrating an exemplary implantable IMD operable to consider cardiac ischemia in electrode selection in accordance with one embodiment.
Figure 2:
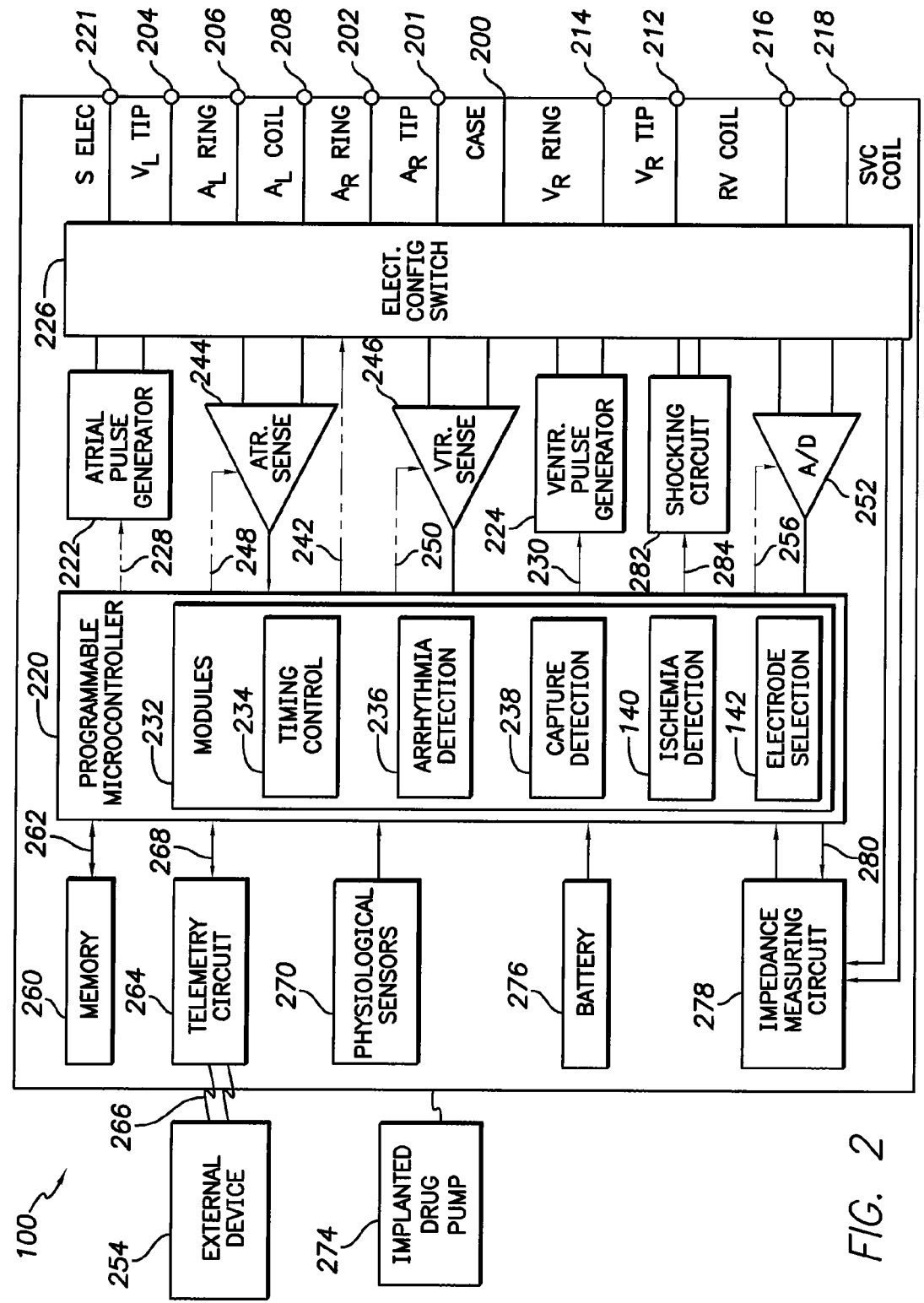
FIG. 2 is a functional block diagram of an exemplary implantable IMD illustrating basic elements that are operable to consider cardiac ischemia in electrode selection in accordance with one embodiment.

The techniques described below can be implemented in connection with any implantable medical device (IMD) that is configured or configurable to sense cardiac data and/or provide cardiac therapy. FIGS. 1-2 collectively describe a first exemplary IMD, while FIG. 3 describes an alternative configuration embodied as a second IMD.

FIG. 1 shows an exemplary IMD 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, IMD 100 includes a fourth lead 110 having, in this implementation, three electrodes 114, 114', 114" suitable for stimulation of autonomic nerves, non-myocardial tissue, other nerves, etc. For example, this lead may be positioned in and/or near a patient's heart or near an autonomic nerve within a patient's body and remote from the heart. In another example, the fourth lead can be configured to sense the phrenic nerve and/or activation of the diaphragm.

The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the IMD 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc. In an alternative configuration, lead 110 can be replaced with a mechanism for connecting the IMD to various other devices. For example, the mechanism can facilitate connecting IMD 100 to a drug pump for dispensing drugs into the patient in accordance with instructions received from the IMD. The skilled artisan should recognize various other configurations that may be employed which are consistent with the principles described above and below.

To sense atrial cardiac signals, ventricular cardiac signals and/or to provide multi-site pacing therapy, particularly on the left side of a patient's heart, the IMD 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

IMD 100 also includes an ischemia detection (ID) module 140 and an electrode selection (ES) module 142. The ischemia detection module 140 detects ischemia in the patient's heart 102. In some cases the ischemia detection module 140 can identify an affected region (introduced by way of example below) of the heart tissue associated with the ischemia or infarct. For example, the ischemia detection module 140 can determine that individual electrodes (and/or other sensors) are sensing the ischemia and therefore are positioned proximate the affected region. The electrode selection module 142 considers the ischemia in selecting electrodes for delivering stimulation therapy. In some scenarios, electrode selection module 142 can enhance a relative effectiveness of stimulation therapy by stimulating between electrodes outside of the affected region because cardiac tissue in the affected region can have diminished responsiveness to stimulation therapy.

For purposes of explanation, consider a hypothetical example where the ischemia detection module 140 detects ischemia by analyzing data sensed by the right ventricular tip electrode 128. The ischemia detection module 140 can further analyze data from other electrodes to determine an extent and/or relative location of the ischemia. In some cases, the ischemia detection module 140 analyzes data from every electrode (122-134) to determine an extent of the ischemia. In another case, the ischemia detection module 140 can analyze data from electrodes proximate the electrode from which the ischemia was initially detected. So, in this example, the ischemia detection module 140 can, for instance, analyze data from the RV ring and coil electrodes 130, 132 and/or the LV tip electrode 122 which are proximate the RV tip electrode 128. Assume further that ischemia is not detected in the data from the RV ring and coil electrodes 130, 132 and/or the LV tip electrode 122. In such an instance, the ischemia detection module 140 can identify an affected region (designated generally at 144) proximate RV tip electrode 128 as being affected by the ischemia. Stated another way, the ischemia detection module 140 can correlate the electrode position to the cardiac tissue to create a map of affected (and unaffected) cardiac tissue.

The electrode selection module 142 can consider region 144 in selecting electrodes for future pacing. For instance, the electrode selection module 142 can select RV ring electrode 130 for future right ventricular pacing rather than RV tip electrode 128. So in one case, stimulation therapy delivered between RV ring electrode 130 and LV tip electrode 122 along a pathway 146 does not pass through affected region 144. Other examples and implementations are described below.

FIG. 2 shows an exemplary, simplified block diagram depicting various components of IMD 100. The IMD 100 can be capable of treating both fast and slow arrhythmias with stimulation therapy, including cardioversion, defibrillation, and pacing stimulation. The IMD can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for IMD 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 201 adapted for connection to the atrial tip electrode 120. A right atrial ring terminal ($A_R$ RING) 202 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the IMD 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller(s) 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes a plurality of modules 232 that, when executed, perform various functions of the IMD. For instance, the modules can perform arrhythmia detection, timing control, and/or morphology detection, among other functionalities.

The illustrated example specifically designates a timing control module 234, an arrhythmia detection module 236, a capture detection module 238, ischemia detection module 140, and electrode selection module 142.

Timing control module 234 controls the timing of the stimulation pulses (e.g., pacing rate, atrio-ventricular (AV) delay, atrial interconduction (A-A) delay, or ventricular interconduction (VV) delay, etc.) as well as to keep track of the timing of refractory periods, blanking intervals, noise detection windows, evoked response windows, alert intervals, marker channel timing, etc., which is well known in the art. The arrhythmia detection module 236 and the capture detection module 238 can be utilized by the IMD 100 for detecting patient conditions and determining desirable times to administer various therapies such as pacing, defibrillation and/or in vivo dispensing of pharmaceuticals.

The ischemia detection module 140 can analyze data sensed by the electrodes 122-134 and/or by various physiological sensors (examples introduced below) to detect cardiac ischemia. In some configurations, the ischemia detection module can detect ischemia and then conduct further analysis to determine an affected region of the heart tissue. In one case, when ischemia is detected by analyzing data from a first electrode, the ischemia detection module 140 can analyze data from other electrodes to determine an extent to which ischemic effects are detected from various electrodes. A similar strategy can be employed when physiological sensors are utilized. Further, the ischemia detection module can employ multiple techniques in detecting ischemia. In one case, the ischemia detection module can detect ischemia from data provided by a physiological sensor (examples introduced below). The ischemia detection module can then analyze data from multiple electrodes to locate an affected region in which the ischemia is occurring.

The ischemia detection module 140 can analyze digitized intracardiac electrogram signals output by the data acquisition system (introduced below) to detect the onset or evolution (i.e. progression or regression) of ischemia and/or infarct. In one embodiment the ischemia detection module 140 compares digitized intracardiac electrogram signals to a baseline template stored in the implanted device to detect myocardial ischemia.

The onset and/or evolution of an ischemic condition can alter the depolarization and repolarization characteristics of the heart. For example, an ischemic region in the ventricle of the heart slows down the propagation of the excitation wave through the ventricles and is evidenced by changes in the QRS complex which models excitation wave propagation through the ventricles. Therefore, one embodiment of the present concepts monitors digitized intracardiac electrograms to detect changes in the morphology of the QRS complex to identify the onset of an ischemic condition. In this embodiment the change in the QRS complex is proportional to the severity of the ischemia.

The electrode selection module 142 can control selection of electrodes based upon their relative proximity to the affected region of cardiac tissue. For instance, if two electrodes are available for pacing the right ventricle, then the electrode selection module 142 can select the electrode that is less proximal to the affected region (i.e., more distal) for pacing via electronic configuration switch 226.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, IMD 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 236 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy.

Advantageously, the operating parameters of the IMD 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The IMD 100 can further include a physiologic sensor(s) 270 to detect one or more of patient activity, patient posture, and respirations, among others. Microcontroller 220 can utilize data received from the physiologic sensor(s) 270 to adjust the various pacing parameters (such as rate, AV Delay, VV Delay, etc.) at which the atrial and ventricular pulse generators, 222 and 224, generate stimulation pulses. Microcontroller 220 further can utilize data received from the physiologic sensor(s) 270 to identify cardiac ischemia. In one such case, the physiologic sensors 270 can include one or more sensors for measuring contractility of various chamber of the heart. Some of these implementations can employ the sensors on one of leads 104-108 to position the sensor in a particular chamber of the patient's heart. The sensors within a heart chamber can allow sensing of the heart's contractility generally and/or of the specific chamber's contractility. The ischemia detection module 140 can analyze the sensed data to determine a region of the heart affected by the ischemia. The electrode selection module 142 can then consider the ischemia when selecting electrodes for stimulation therapy. For instance, electrode selection module 142 can select an electrode(s) to pace around the affected region.

While shown as being included within the IMD 100, it is to be understood that the physiologic sensor 270 may also be external to the IMD 100, yet still be implanted within or carried by the patient. Examples of physiologic sensors that may be implemented in IMD 100 include known sensors that, for example, sense pressure, respiration rate, pH of blood, cardiac output, preload, afterload, contractility, oxygen levels, and so forth. Another sensor that may be used is one that detects activity variance, where an activity sensor is monitored to detect the low variance in the measurement corresponding to the sleep state and/or maintenance of a specific posture.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's posture and activity status, such as whether the patient is climbing upstairs or descending downstairs or whether the patient is sitting up after lying down.

The IMD 100 optionally includes circuitry capable of sensing heart sounds and/or vibration associated with events that produce heart sounds. Such circuitry may include an accelerometer as conventionally used for patient position and/or activity determinations.

While an accelerometer may be included in the case of an IMD in the form of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

IMD 100 may also include, or be in communication with, an implanted drug pump 274 or other drug delivery mechanism to effect patient therapy. The drug pump can be activated in various scenarios, such as when a heart failure condition is detected.

The IMD 100 additionally includes a battery 276 that provides operating power to all of the circuits shown in FIG. 2. For the IMD 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The IMD 100 can further include magnet detection circuitry (not shown), coupled to the microcontroller 220, to detect when a magnet is placed over the IMD 100. A magnet may be used by a clinician to perform various test functions of the IMD 100 and/or to signal the microcontroller 220 that the external programmer 254 is in place to receive or transmit data to the microcontroller 220 through the telemetry circuits 264. Trigger IEGM storage also can be achieved by magnet.

The IMD 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance, such as for determining shock thresholds, (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the IMD 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize battery drain and the more rapid delivery of the shock if the lower energy levels are effective in restoring a normal rhythm), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an IMD typically delivers a cardioversion stimulus (e.g., 0.1-5 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
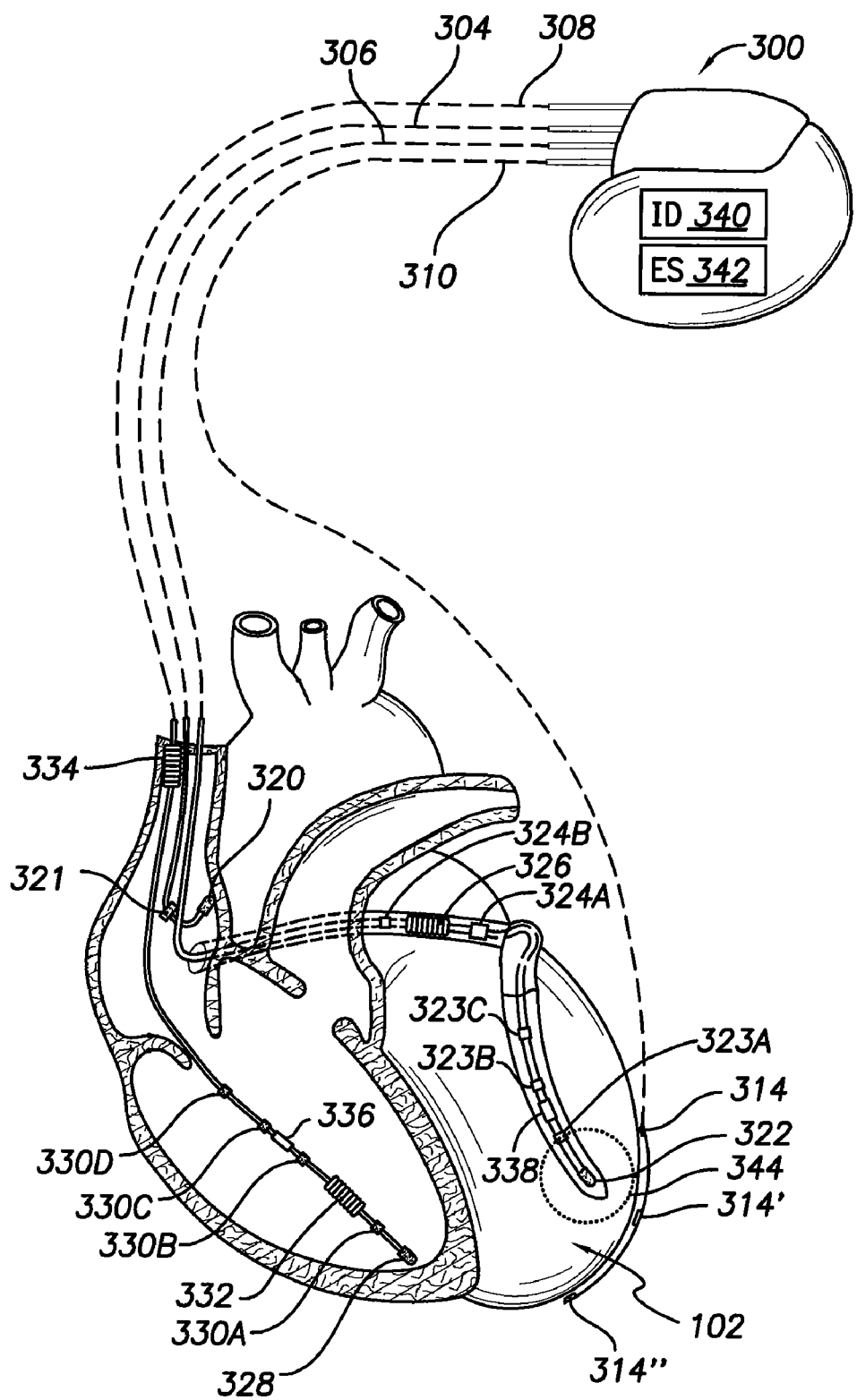
FIG. 3 is a simplified diagram illustrating another exemplary implantable IMD operable to consider cardiac ischemia in electrode selection in accordance with one embodiment.

FIG. 3 shows an exemplary IMD 300 that is similar to IMD 100 described above in relation to FIGS. 1-2 though IMD 300 offers an increased number of pacing options relative to IMD 100. In this instance, IMD 300 is in electrical communication with a patient's heart 102 by way of three leads 304, 306, 308, suitable for delivering multi-chamber stimulation and shock therapy. In addition, IMD 300 includes a fourth lead 310 having, in this implementation, three electrodes 314, 314', 314" suitable for epicardial positioning.

The right atrial lead 304 is positioned in and/or passes through a patient's right atrium. The right atrial lead 304 optionally senses atrial cardiac signals and/or provides right atrial chamber stimulation therapy. As shown in FIG. 3, the IMD 300 is coupled to an implantable right atrial lead 304 having an atrial tip electrode 320, which typically is implanted in the patient's right atrial appendage. The lead 304 also includes an atrial ring electrode 321.

To sense atrial cardiac signals, ventricular cardiac signals and/or to provide multi-site pacing therapy, particularly on the left side of a patient's heart, the IMD 300 is coupled to a coronary sinus lead 306 designed for placement in the coronary sinus and/or tributary veins of the coronary sinus. Thus, the coronary sinus lead 306 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 306 is optionally designed to receive atrial and ventricular cardiac signals and to deliver left ventricular pacing therapy. In this instance, left ventricular pacing therapy can be delivered via one or more of a left ventricular (LV) tip electrode 322, a first left ventricular ring electrode 323A, a second left ventricular ring electrode 323B, and a third left ventricular ring electrode 323C. Alternatively or additionally, left ventricular pacing can be delivered via one or more of electrodes 314, 314', and 314". Left atrial pacing therapy can be delivered via first and second left atrial ring electrodes 324A, 324B. Left atrial shocking therapy can be delivered using at least a left atrial coil electrode 326.

IMD 300 is also shown in electrical communication with the patient's heart 102 by way of an implantable right ventricular lead 308 having, in this exemplary implementation, a right ventricular tip electrode 328, a first right ventricular ring electrode 330A, a second right ventricular ring electrode 330B, a third right ventricular ring electrode 330C, a fourth right ventricular ring electrode 330D, a right ventricular (RV) coil electrode 332, and an SVC coil electrode 334. Typically, the right ventricular lead 308 is transvenously inserted into the heart 302 to place the right ventricular tip electrode 328 in the right ventricular apex so that the RV coil electrode 332 will be positioned in the right ventricle and the SVC coil electrode 334 will be positioned in the superior vena cava. Accordingly, the right ventricular lead 308 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

IMD 300 further includes a first contractility sensor 336 employed on lead 308 in the right ventricle and a second contractility sensor 338 employed on lead 306 in the left ventricle. The contractility sensors can provide information relating to the pumping efficiency of tissues in the respective right and left sides of the heart. Other implementations can employ more, fewer or different types of sensors. For instance, one implementation can employ multiple contractility sensors in an individual heart chamber to provide data relating to the pumping efficiency of particular regions of the surrounding heart tissue.

IMD 300 also includes an ischemia detection module (ID) 340 and an electrode selection (ES) module 342. The ischemia detection module 340 detects cardiac ischemia or infarct in a region of the heart tissue proximate one of leads 304, 306, 308, and 310. For instance, in a first scenario, assume that IMD 300 is accomplishing left ventricular pacing via left ventricular tip electrode 322. The IMD can periodically analyze intracardiac electrogram (IEGM) data from each of the pacing electrodes in the left ventricle (i.e., 322, 323A-323C).

In a hypothetical scenario, consider that ischemia detection module 340 analyzes IEGM data from the left ventricular tip electrode 322 and detects a change in the IEGM data indicative of ischemia. Consider further that ischemia detection module 340 detects a similar but less significant change in IEGM data from left ventricular ring electrode 323A and no ischemia from the IEGM data from left ventricular ring electrodes 323B and 323C. The ischemic detection module 340 can identify an ischemic or affected region 344 of the left ventricle as being generally centered around the LV tip electrode 322 and extending toward LV ring electrode 323A, but not extending to LV ring electrodes 323B, 323C. Another implementation for detecting the ischemic region can utilize changes detected in the data collected by one or more of the contractility sensors 336, 338 to identify affected region 344 or as a trigger to analyze data collected from one or more electrodes to identify the affected region and/or to verify the ischemia.

The electrode selection module 342 can consider the ischemia data from the ischemic detection module 340 in selecting stimulation electrodes. For instance, electrode selection module 342 can select one or both of LV ring electrodes 323B, 323C for future pacing therapy to the left ventricle rather than LV tip electrode 322 or LV ring electrode 323A.

In another case, the electrode selection module 342 can address the ischemic region 344 by pacing through all of the left ventricular electrodes 322, 323A, 323B, and 323C to enhance a likelihood that adequate pacing is achieved. In still another instance, the electrode selection module can pace between electrodes on the LV lead 306. For instance, the electrode selection module can pace from LV tip electrode 322 to LV ring electrode 323A and/or from LV ring electrode 323B to LV ring electrode 323C, among others. Alternatively or additionally, the electrode selection module can select electrodes on other leads to avoid the ischemic region 344. For instance, one or more electrodes (314, 314', and/or 314") of lead 310 positioned in the epicardium can be selected. In the illustrated example, electrodes 314 and 314" could be selected for pacing as they are less affected by ischemic region 344 than electrode 314'.

Further still, the electrode selection module 342 can compare the available electrodes via one or more criteria to select a pacing electrode(s). For instance, in the above scenario where the LV tip electrode 322 is proximate the ischemic region 344 the electrode selection module can determine the available electrodes. Assume for purposes of example that the determined available electrodes are the LV ring electrodes 323A, 323B, and 323C and the epicardial electrodes 314, 314', and 314". The electrode selection module can utilize various criteria to determine which of the available electrodes to select for pacing. Non-limiting examples of the criteria can include conduction parameters, hemodynamic parameters, and IEGM parameters.

An example of a conduction parameter is the conduction time between individual available electrodes and another different reference electrode. In one case, the electrode selection module can utilize RV tip electrode 328 as the reference electrode and can compare conduction times between each of the individual available electrodes and the RV tip electrode. Generally, healthy cardiac tissue has faster conduction times compared to unhealthy cardiac tissue (i.e., ischemic tissue). Therefore, over similar distances shorter conduction times can reflect conduction pathways through healthy cardiac tissue. Thus, the electrode selection module can select the pacing electrode from the available electrodes based at least in part upon the conduction rate.

One example of determining hemodynamic parameters can be to sequentially pace through each of the available electrodes and measure the corresponding cardiac output. The electrode selection module can then select the pacing electrode that produces the highest cardiac output. Similarly, IEGM data can be studied during this sequential pacing process. The IEGM results can be compared to determine which available electrode to select for pacing. For instance, an individual available electrode that produces the highest peak-to-peak amplitude can be selected over other available electrodes that produce lower amplitudes. For purposes of explanation the above example compares and selects individual available electrodes, but other implementations may select multiple electrodes for pacing. For example, the electrode selection module can select two of the available electrodes for pacing. For instance, assume that in the above example, electrodes 323B and 314 produced better results than the other available electrodes, then the electrode selection module can select to pace between both electrodes 314 and 323B and the RV tip electrode 328. The skilled artisan should recognize other parameters and/or combinations of parameters that can be utilized to determine which electrode (s) to select for pacing.

The electrode selection module 342 can utilize the ischemia information to provide more effective pacing therapy to the patient in many ways. As mentioned above, the electrode selection module 342 can pace away from the region of ischemic heart tissue (I.e., to healthy heart tissue). Alternatively or additionally, in some implementations the electrode selection module 342 can pace between an ischemic region and an unaffected region. For instance, continuing with the above example the electrode selection module 342 can pace between LV tip electrode 322 in the affected ischemic region 344 and LV ring electrode 323C that is in a non-affected region (i.e., outside the affected region). The concepts described in relation to FIGS. 1-3 and the discussed implementations can also be implemented in a multitude of other implementations as should be recognized by the skilled artisan.

Exemplary Ischemia Detection Techniques

Many ischemia detecting techniques can be employed with the concepts described above and below. For instance, various ischemia detection techniques are discussed in U.S. Pat. No. 6,604,000 to Lu which is incorporated by reference herein. FIGS. 4-8 provide examples of several ischemia detection techniques that are described below in more detail.

Figure 4:
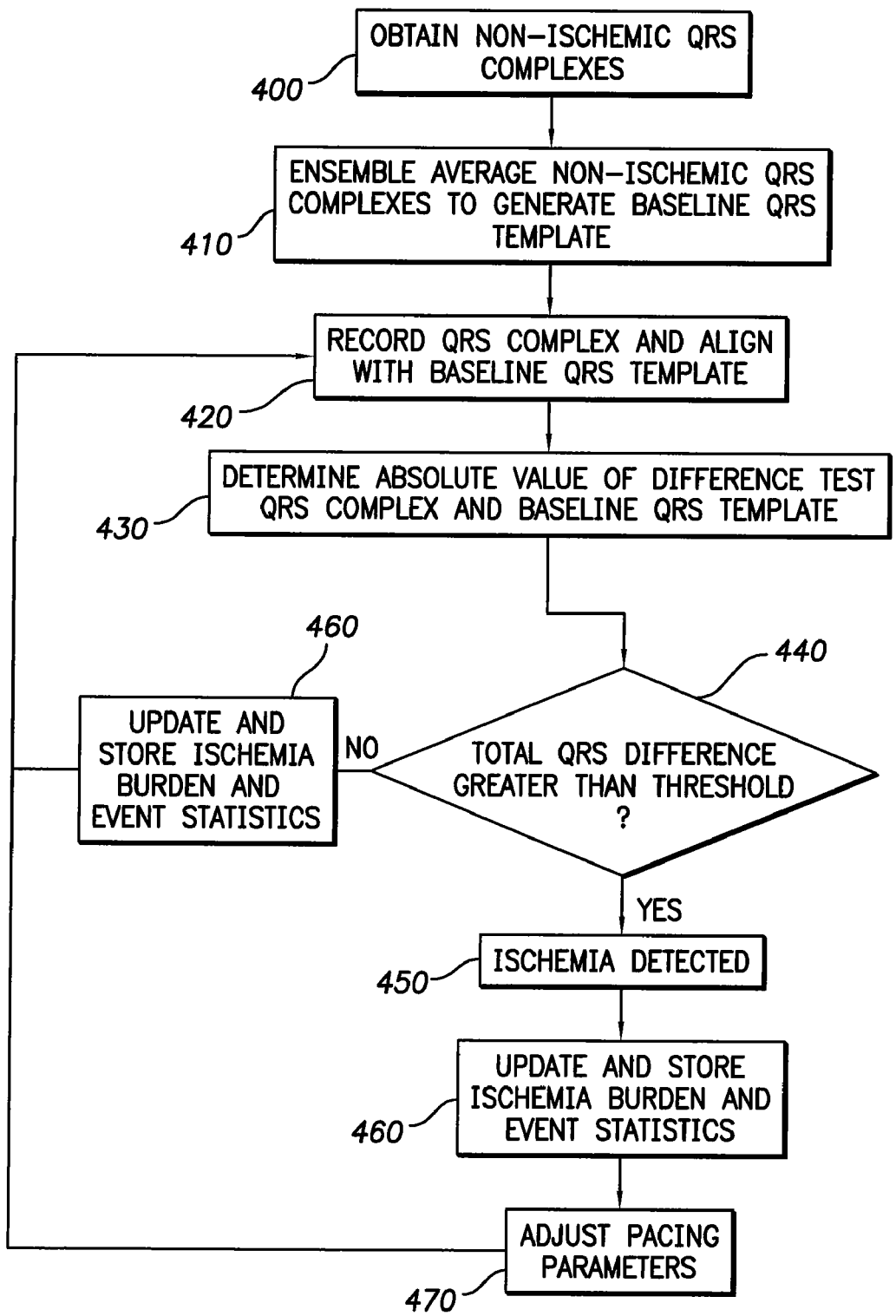
FIG. 4 is a flow chart illustrating a method to detect ischemia in accordance with one embodiment.
Figure 5:
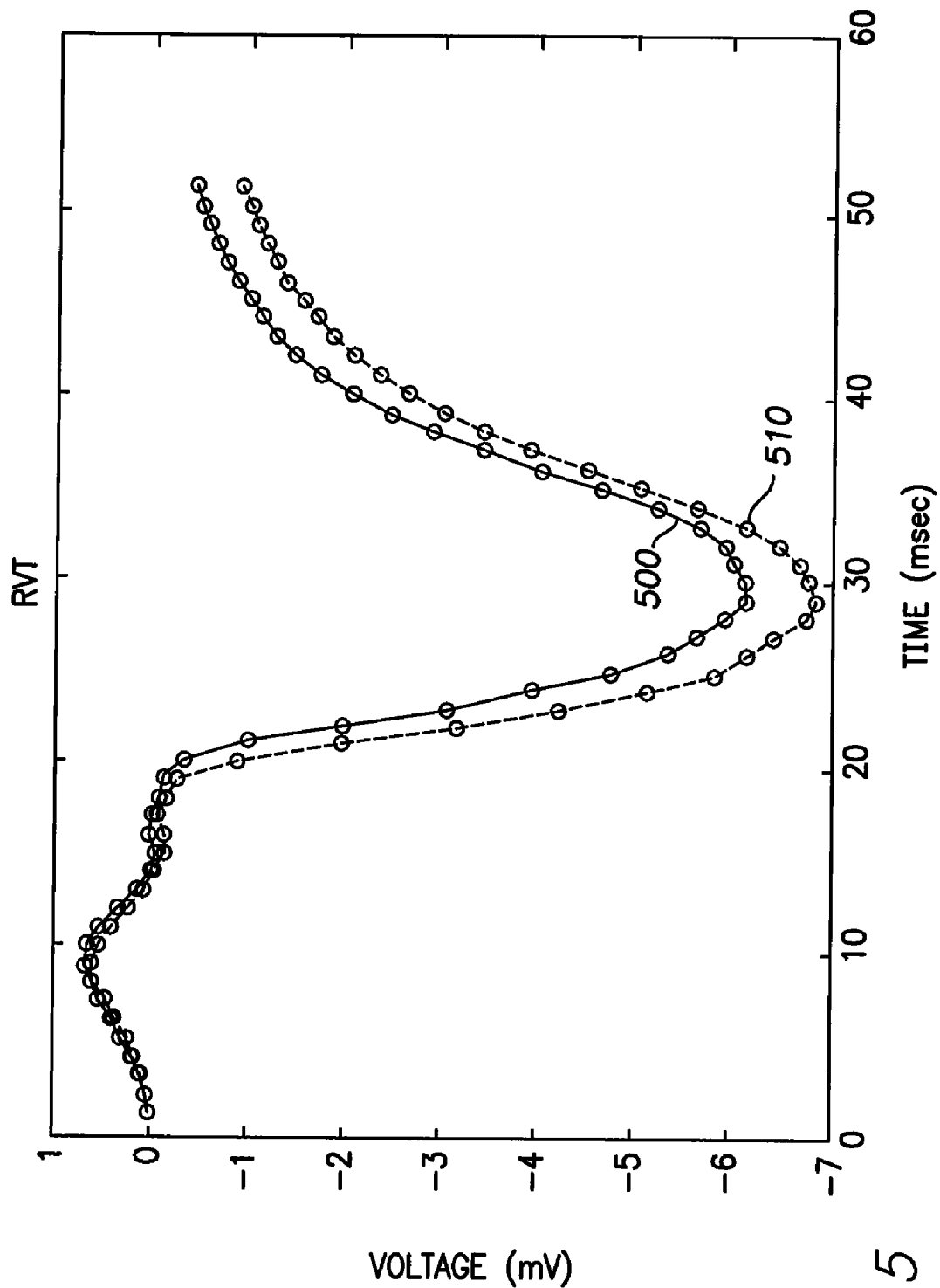
FIG. 5 is a graphical illustration of a baseline QRS complex and an ischemic QRS complex resulting from a forced occlusion.
Figure 6:
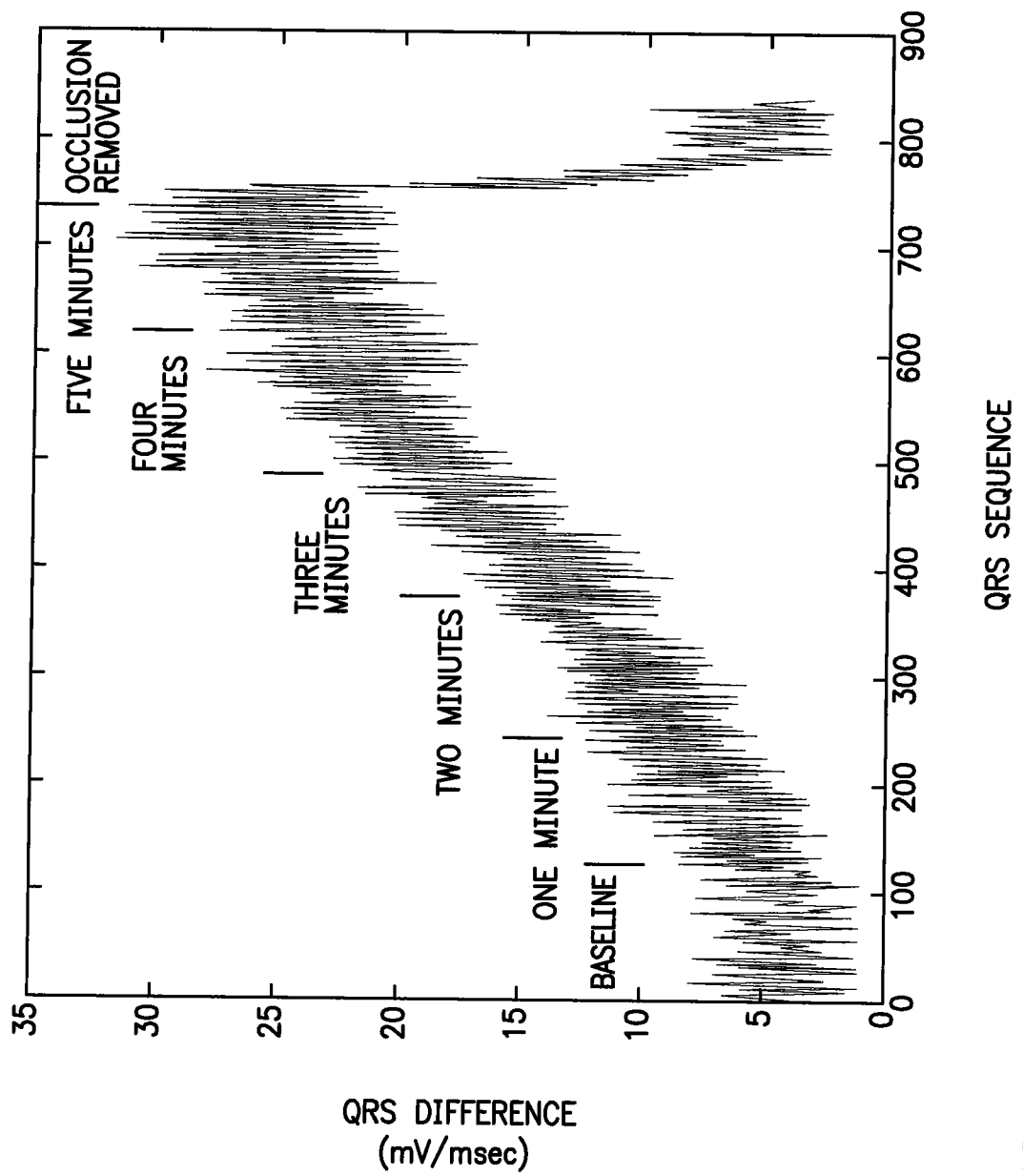
FIG. 6 is a graphical illustration of the total QRS difference between a baseline QRS complex and an ischemic QRS complex resulting from a forced occlusion as a function of length of the occlusion.
Figure 7:
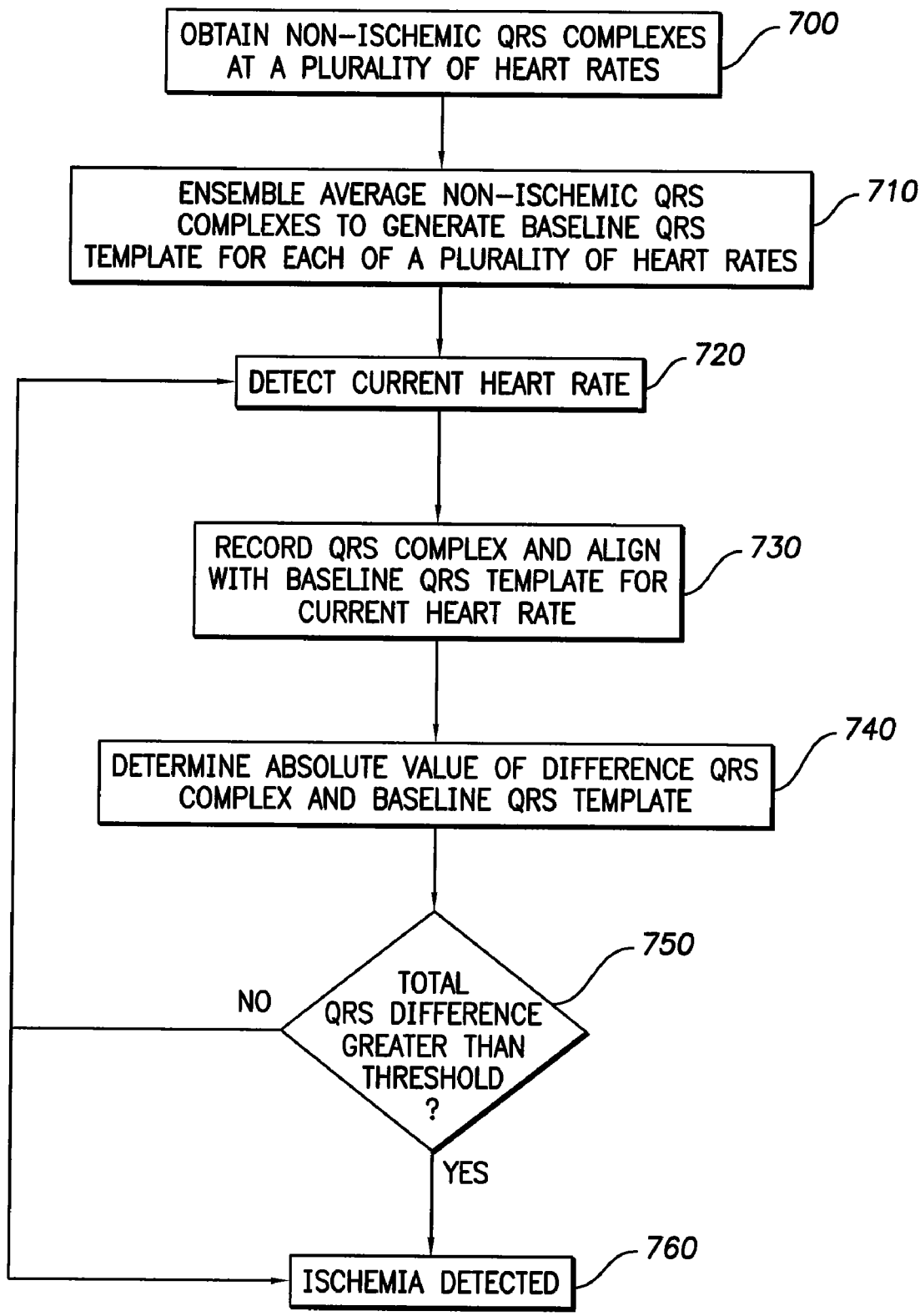
FIG. 7 is a flow chart illustrating a method to detect ischemia over a range of heart rates in accordance with one embodiment.

FIG. 4 is a flowchart illustrating the operation of one embodiment of a stimulation device to detect the onset or progression of ischemia as a function of changes in the amplitude of the voltage of the QRS complex. In this flow chart, the various operational steps are summarized in individual "blocks". Such blocks describe specific actions or decisions that are carried out during operation of the illustrated IMD 100 and/or IMD 300. Where a microcontroller (or equivalent) such as microcontroller 220 described above in relation to FIG. 2 is employed, the flow chart presented herein provides the basis for a "control program" that may be used by such a microcontroller (or equivalent) to effectuate the desired control of the stimulation device.

In one embodiment of the present invention the microcontroller, either automatically or under the control of the treating physician, records a plurality of digitized baseline (non-ischemic) QRS complexes 400. Various digital signal processing techniques may be employed for the analysis, such as using first and second derivatives to identify the start and end of the QRS waves.

In one embodiment the complexes are typically recorded for a pre-determined time period beyond the onset of the Q-wave. In this embodiment the microcontroller aligns the maximum amplitude points of the recorded complexes and calculates an ensemble average of the time sampled complexes to generate a baseline QRS template which is stored in memory 410 for subsequent comparison purposes.

The present invention utilizes both paced and intrinsic events to detect an ischemic condition. Therefore, in some embodiments the microcontroller generates separate baseline QRS templates for paced and intrinsic events. In these embodiments, paced and intrinsic measurements are not combined to generate a baseline template but are evaluated separately.

In operation the micro-controller then periodically performs an ischemic test by recording a digitized paced or intrinsic ventricular depolarization (e.g. QRS complex) for comparison to the appropriate paced or intrinsic baseline QRS template. In one embodiment the microcontroller aligns the maximum amplitude of the baseline QRS template with the maximum amplitude of the QRS complex under test 420. Alternatively, the microcontroller may record a plurality of consecutive or nearly consecutive QRS test complexes and ensemble average the recorded plurality of test complexes which is then used in the comparison test.

The microcontroller then determines, by way of example, the absolute value of the difference in voltage amplitude at each of the sample points of the digitized QRS complexes 430. For example, FIG. 5 graphically compares the ensemble average of multiple baseline (non-ischemic) QRS complexes 500 measured on a unipolar right ventricular tip (RVT) electrode in a canine with an ischemic QRS complex 510 measured on the same electrode as a function of time. In this instance the ischemic QRS complex was recorded approximately five minutes into the occlusion of the proximal region of the left arterial descending artery (LAD) of the canine. The effects of the occlusion on the propagation of the excitation wave through the ventricles are seen in the variation between the voltage of the ischemic QRS complex and the voltage of the baseline complex.

Further, the magnitude of the change in voltage provides an indication of the severity of the ischemic condition. For example, FIG. 6 graphically illustrates the trend of the total QRS difference values (i.e. the sum of the absolute value of the difference at each of the sample points of a digitized baseline complex and an ischemic complex) for a series of QRS complexes over the course of a five minute forced occlusion of the proximal region of the left arterial descending artery (LAD) of a canine. The measured data was again collected on a unipolar right ventricular tip (RVT) electrode in the canine.

In this example, there is relatively little difference between the baseline QRS (i.e. no occlusion shown for approximately the first 110 sequences) and the stored QRS template. However, the total QRS difference between baseline and ischemic complexes gradually increases as the duration of the occlusion increases, reaching a maximum of approximately 30 mVms at the end of five minutes. In this illustrative example the occlusion was removed after five minutes and the QRS difference converges relatively quickly to the non-ischemic values.

Returning to FIG. 4, in one embodiment the microcontroller therefore sums the absolute value of the difference at each sample point of the baseline QRS templates and a single QRS complex and compares the total QRS difference to a programmable threshold 440. If the total QRS difference is greater than the programmable threshold value ischemia is detected at 450. In one embodiment of the invention the QRS template is not redefined or updated after ischemia is detected to allow for the documentation of the long term progression of the ischemic burden.

Alternatively, the microcontroller can calculate the total QRS difference for each of several consecutive or approximately consecutive QRS complexes. In this embodiment the microcontroller calculates various statistics, such as, by way of example, the statistical mean, variance and the like, of the total QRS differences and compares the mean or variance of the total QRS difference to a threshold to detect the onset of ischemia.

The ischemia detection threshold is, by way of example, programmable and may vary depending upon the application, patient condition and physician preference. Further the interval at which ischemia diagnoses are performed also depends on the application.

For example, in some embodiments the microcontroller measures the ischemia burden approximately every one to two hours to generate a long-term diagnostic record. In this instance the microcontroller records a QRS complex every hour and compares the digitized QRS complex to a baseline QRS template determined at a single point in time (e.g. at implant or at the command of a clinician). Alternatively, the long term ischemic burden may be monitored by determining the total difference value for the recorded complex and a baseline QRS template in the form of an average of a plurality of baseline QRS templates recorded over a relatively long period of time (e.g. a long term moving average taken over the previous week).

In the context of acute ischemia event detection, the microcontroller in one embodiment determines the total QRS difference on a more regular basis, for example, approximately every 30-60 seconds. In this context, the microcontroller determines the baseline QRS template from a relatively recent history. For example, in some embodiments the microcontroller computes the baseline QRS template from a short term moving average of QRS complexes periodically measured over the previous hour.

In this instance acute myocardial ischemia is indicated if the calculated total QRS difference between the QRS complex under test and the baseline template exceeds a programmable threshold. In some embodiments an ischemic event is detected if only one QRS difference measurement exceeds the threshold. In other embodiments the detection of an ischemic event requires several consecutive complexes (e.g. 3-5) having a total QRS difference value that exceeds the threshold. Alternatively ischemia detection may require that the total QRS difference value for a predetermined percentage (e.g. 3 out of 5) of consecutive QRS complexes exceed the threshold.

Further, in some embodiments the microcontroller utilizes a measure of statistical significance (e.g. T-statistic) between the baseline and subsequent measurements compared to a threshold to verify the detection of an ischemic event using the total QRS difference value. Similarly, in other embodiments the microcontroller monitors the width of the QRS complex and verifies ischemia detection if the width of the complex under study is greater (by a predetermined amount of time) than the baseline QRS template or greater than a threshold value.

A long-term record of the patient's ischemia burden obtained through continuous monitoring is a useful adjunct to current methods of ischemia detection and diagnosis. Such a record may reveal infrequent or unprovokable ischemia perhaps associated with nascent coronary artery disease, vasospasm or embolism as well as trends in the progression or regression of coronary artery disease. A long-term record of ischemia burden can also be used to gauge the efficacy of, and/or patient compliance with, a course medication.

Therefore, in one embodiment, the microcontroller generates an ischemia burden metric for tracking the evolution of the ischemia. The burden metric in one embodiment is the ratio of periodic measurements for which ischemia is indicted relative to the total number of periodic measurements. In this embodiment the microcontroller stores and updates the ischemia burden, and any other clinically significant event statistics such as the total QRS difference, heart rate, activity rate, or the like in device memory upon completion of the ischemia diagnostic test 460.

In some embodiments the ischemia burden metric includes an indication of the certainty of the detection and/or the severity of the ischemia. In one embodiment for example, the degree by which a feature exceeds its threshold for ischemia detection is mapped to a severity/likelihood index. In some embodiments, low value for the severity/likelihood index values indicate the threshold for detection was barely exceeded and high values indicate the threshold was exceeded by at least a predetermined percentage. In these embodiments the burden metric tracks the number of ischemia event detections and the severity level of each detected event.

The event log and/or the recorded electrogram exhibiting the ischemia may be downloaded at a later time to a clinician for analysis via an external programmer. The clinician is then able to use this information in making subsequent treatment decisions.

Ischemia is a condition resulting from insufficient blood flow through the heart muscle. Because myocardial perfusion occurs primarily during the diastolic phase, lower heart rates, which have correspondingly longer diastolic phase, are conducive to increased perfusion while high heart rates have the potential of exacerbating an ischemic condition. Therefore, in some embodiments the microcontroller automatically adjusts the pacing mode or pacing parameters in response to the detection of an ischemic condition to ensure that the heart is not paced at a rate that might worsen the ischemic effects 470.

For instance, in one embodiment the microcontroller automatically switches to a non-tracking pacing mode in response to the detection of an ischemic condition. Alternatively, the microcontroller may adjust various pacing parameters in response to the detection of an ischemic condition. For example, in one embodiment the microcontroller automatically decreases the maximum tracking rate to limit the rate at which the ventricles can be paced regardless of the atrial rate to ensure that the heart is not paced at a rate that exacerbates the ischemic condition.

The microcontroller may also automatically adjust the maximum pacing rate during rate-adaptive pacing in response to the detection of cardiac ischemia. Typically, a rate responsive cardiac stimulation device increases its pacing rate (up to a maximum sensor rate) in response to increases in the patient's activity level. The rate of this change is referred to as the aggressiveness of the rate response.

However, in an ischemic state, the aggressiveness of the rate response may provide for a pacing rate that exacerbates the ischemic effects. Accordingly, in some embodiments of the present invention the microcontroller adaptively reduces the maximum sensor rate or increases the atrio-ventricular (AV) delay in response to the detection of an ischemic state.

In addition, in some embodiment, the implantable device forces the ventricular rate lower than the sinus rate through special pacing techniques such as the one described in commonly owned U.S. Pat. No. 6,377,852, entitled "Implantable Cardiac Stimulation Device And Method For Prolonging Atrial Refractoriness" by Bornzin, Sloman, Boileau and Florio, the content of which is incorporated herein by reference as if set forth in full. Conversely, when an ischemic state is no longer detected, the adapted variables are incrementally returned toward its original value. Accordingly, ischemia can be minimized while still maintaining the rate responsive features of the implantable cardiac stimulation device.

One of skill in the art will appreciate that the sample length and sampling rate used to generate the QRS complexes can affect the performance of the classification system. For example, varying the sampling rate creates tradeoffs between the response time of the detection system and the sensitivity and specificity of the detection system as well the computational duty cycle of the detection algorithm.

Further the QT interval typically varies with heart rate. Therefore in some embodiments, the micro-controller adjusts the pacing therapy to provide appropriate conditions for the diagnosis for ischemia. For example, the microcontroller may invoke AV hysteresis (i.e. lengthening or shortening of the AV delay) to encourage V-pacing or inhibition if primarily paced or intrinsic events are desired for the ischemia diagnosis. In a ventricular resynchronization therapy device, V-V timing may also be adjusted.

Similarly, the microcontroller may slow the pacing rate to a target rate if it is currently elevated, e.g. due to rate response for activity level. Further, the pacing rate may be slightly increased to a target rate temporarily to provoke ischemia in case myocardial oxygen demand is on the verge of exceeding supply.

In some embodiments the microcontroller optionally confirms that favorable conditions for ischemia detection exist and if not, e.g. if the intrinsic rate is too fast, a measurement is not made at this time. Rather the existence of unfavorable conditions is optionally logged.

In other embodiments the microcontroller normalizes the QRS difference values as a function of heart rate to provide ischemia diagnostic capability over a range of heart rates. For example, referring to the flow chart in FIG. 7, in one embodiment of the present invention the microcontroller, either automatically or under the control of the treating physician, records a plurality of digitized (non-ischemic) QRS complexes 700 at each of a plurality of heart rates. In this embodiment, digital signal processing techniques, such as, by way of example, first and second derivative calculations, may again be used to identify the start and end of the QRS waves at each of the plurality of heart rates.

In one embodiment the complexes are typically recorded for a pre-determined time period beyond the onset of the Q-wave for each of the plurality of heart rates in accordance with the variation of the QRS width as a function of heart rate. In this embodiment the microcontroller calculates an ensemble average of the time sampled complexes for each of the plurality of heart rates to generate a baseline QRS template for each heart rate which is stored in memory 710 for subsequent comparison purposes.

When performing an ischemic test the device first determines the current heart rate 720 then records a digitized QRS complex for comparison to the stored baseline QRS complex corresponding to the current heart rate. In one embodiment the microcontroller aligns the maximum amplitude of the baseline QRS template with the maximum amplitude of the QRS complex under test 730.

The microcontroller then determines, by way of example, difference of the amplitude of the voltage at each sample point of the QRS complexes 740. The microcontroller then sums the absolute value of the difference at each sample point and compares the total QRS difference to a programmable threshold 750. If the total QRS difference is greater than the programmable threshold value ischemia is detected at 660.

In other embodiments the microcontroller utilizes multiple sensing vectors (e.g. RV ring to case, LV ring to case, or the like) to improve sensitivity and/or specificity. In some instances multi-site characterization provides the ability to reveal a pattern unique to ischemia and different from patterns which might be produced by other confounding influences. In addition, multi-site measurements provide a rough indication of the location of the occlusion in the heart.

Figure 8:
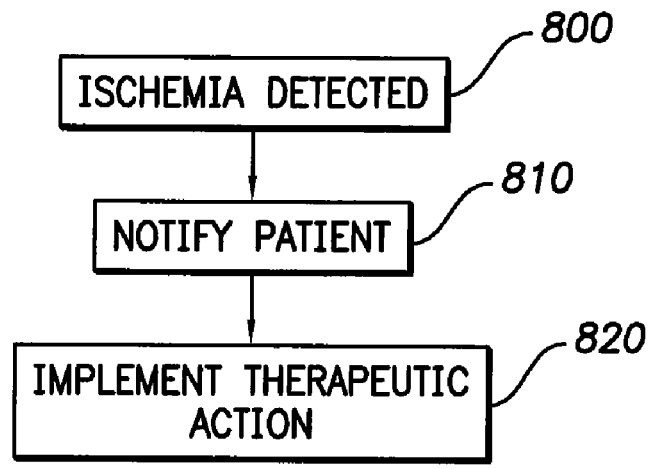
FIG. 8 is a flow chart illustrating a method for responding to the detection of an ischemic event in accordance with one embodiment.

Referring to FIG. 8, in some embodiments of the present invention upon detection of an ischemic condition at 800 an implantable stimulation device may instigate various actions. For example, as mentioned above and below, some implementations can alter a pacing therapy to pace away from a region of the heart associated with the ischemia.

Exemplary Methods

Figure 9:
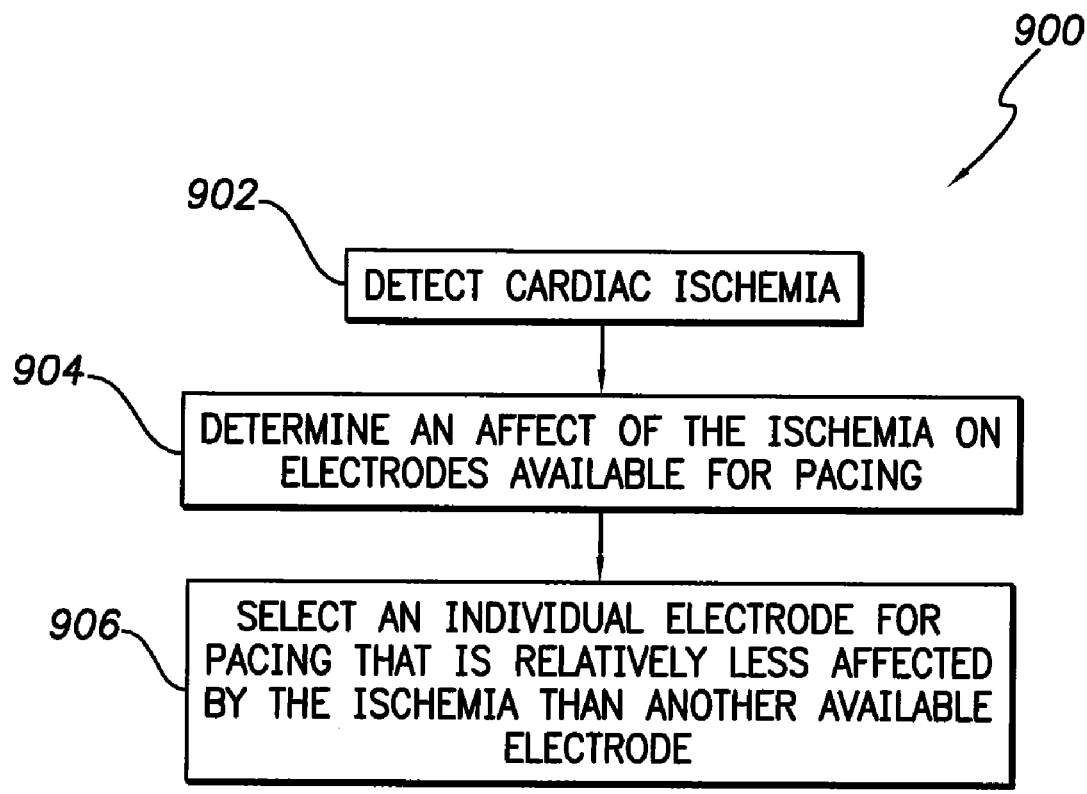
FIG. 9 is a flowchart of an exemplary method for considering cardiac ischemia in electrode selection in accordance with one embodiment.

FIG. 9 shows an exemplary method or technique 900 for considering cardiac ischemia in electrode selection. This method 900 may be implemented in connection with any suitably configured implantable medical devices (IMDs) and/or systems such as those described above. Method 900 includes blocks 902-906. The order in which the method is described is not intended to be construed as a limitation, and any number of the described blocks can be combined in any order to implement the method, or an alternate method. Furthermore, the method can be implemented in any suitable hardware, software, firmware, or combination thereof such that a computing device can implement the method. In one such instance, a computing device in the form of an IMD, implements some or all of the method. The method can be stored as a set of instructions on a computer readable storage media. The instructions can cause a computing device to implement the method.

At block 902, cardiac ischemia is detected. Many techniques are available for detecting cardiac ischemia. Several examples are described above. For instance, sensed IEGM data can be analyzed to detect ischemia. Other techniques include detecting changes in the heart's pumping efficiency such as by measuring contractility and/or detecting impedance changes in the cardiac tissue. Still another ischemia detection technique utilizes a rate of conduction through the cardiac tissue as ischemic tissues tend to conduct slower than healthy tissue.

At block 904, an affect of the ischemia on electrodes available for stimulation and/or pacing is determined. Stated another way, is an individual electrode positioned adjacent to cardiac tissue experiencing ischemia and/or will the electrode pace through cardiac tissue experiencing ischemia? In some implementations, the affect is determined on a lead by lead basis. For instance, consider a hypothetical scenario where pacing is conducted between an electrode on a first lead and an electrode on a second lead. Assume further that the first lead has four available electrodes AA, BB, CC, and DD and that the second lead has three available electrodes EE, FF, and GG. In this scenario the method can be applied to one or more of electrodes AA, BB, CC, and DD from the first lead and electrodes EE, FF, and GG from the second lead to determine which if any electrodes are affected by the ischemia. In another scenario assume that pacing occurs between an electrode(s) of the first lead and a "housing" of the IMD. In this scenario the method can be applied to the electrodes AA, BB, CC, and DD of the first lead to determine which if any of the electrodes are affected by the ischemia and/or that a signal delivered between an individual electrode and the housing would pass through affected cardiac tissue. Other implementations may not consider the electrodes relative to leads, but may instead look for electrodes available for a particular pacing therapy. For instance, the method can be applied to electrodes available for pacing between the left ventricle and the right ventricle regardless of what leads the available electrodes reside upon.

In some instances, the technique(s) utilized to detect the ischemia may lend itself to determining the proximity of the ischemic or affected region of tissue to the electrode(s). For example, in one scenario, individual contractility sensors can be positioned on a lead adjacent individual electrodes. In such a scenario, an individual contractility sensor(s) that detects the ischemia can be correlated to individual adjacent electrodes. The adjacent electrodes are more likely to be positioned proximate affected cardiac tissue than more distal electrodes. In other instances, detecting the ischemia and determining the affect of the ischemia on the available electrodes can be accomplished by the same act. For instance, some implementations can periodically obtain IEGM data from multiple electrodes and analyze the IEGM data to detect ischemia relative to an individual electrode. Correspondingly, in an instance where ischemia is detected from IEGM data from one or more electrodes, then the location of the ischemia relative to the electrode is also thereby determined.

In another instance, the method can test one or more of the available electrodes for affects of the ischemia. For instance, IEGM data can be sensed from each available electrode. The IEGM data from each electrode can be analyzed to detect affects of the ischemia and/or to detect the extent of the ischemic affects. In a particular scenario, the ischemia can be detected by periodically analyzing IEGM data from an electrode that is currently selected for pacing. For instance, consistent with the above example assume that a current pacing regime is between electrode AA of the first lead and electrode FF of the second lead. In some implementations, the method can periodically analyze IEGM data from electrodes AA and FF. In an instance where ischemia is detected from one or more currently selected electrodes then IEGM data can be gathered and sensed from other available electrodes. So, continuing with the above example, if ischemia is detected from IEGM data from either or both of electrodes AA and FF then the method can analyze IEGM data from all of the available electrodes AA-GG. Comparison of the IEGM analysis from the available electrodes can identify which electrodes are adjacent regions of the heart that are affected by the ischemia and to what extent individual adjacent regions are affected. In this way, the method can serve to map the location of the ischemia relative to the electrodes. So in the above example, assume that ischemia is initially detected from IEGM data gathered from electrode AA and that analysis of IEGM from each of the electrodes (AA-GG) detects ischemia only from electrode AA and to a lesser extent electrode BB. The method can then determine that a region of cardiac tissue affected by the ischemia is generally proximate electrode AA and extends at least to some extent toward electrode BB.

At block 906, an individual electrode is selected for stimulation that is relatively less affected by the ischemia than another available electrode. Stated another way, an electrode is selected that is relatively more distant the region of affected or ischemic cardiac tissue. Pacing therapy can be more effective when delivered to healthy cardiac tissue rather than ischemic tissue. In the case of the above hypothetical example where ischemia was detected proximate electrode AA and BB then the method can select either of unaffected electrodes CC and DD for pacing with any of electrodes EE-GG. In an instance where the first lead included only electrodes AA and BB then electrode BB can be selected as electrode BB is less affected by the ischemia than electrode AA. Selection of an individual electrode does not necessarily mean selecting only one electrode. For instance, in the above example the method can select individual electrode CC and individual electrode DD and pace between both electrodes CC and DD and one or more of electrodes EE-GG.

Selecting a pacing and/or stimulation electrode that is relatively less affected or unaffected by ischemia can provide a more effective patient treatment and as such contributes to overall patient well-being. The skilled artisan should recognize variations consistent with these concepts.

CONCLUSION

Although exemplary techniques, methods, devices, systems, etc., have been described in language specific to structural features and/or methodological acts, it is to be understood that the subject matter defined in the appended claims is not limited to the specific features or acts described. Rather, the specific features and acts are disclosed as exemplary forms of implementing the claimed methods, devices, systems, etc.

What is claimed is:

1. An implantable medical device (IMD) comprising:
   an ischemia detection module for detecting cardiac ischemia or infarct in a region of cardiac tissue proximate a multiple-electrode lead, wherein the ischemia detection module is operable to evaluate intracardiac electrogram (IEGM) data from each electrode on the multiple-electrode lead to detect the relative proximity of the cardiac ischemia or infarct region from each electrode of the multiple electrode lead; and
   an electrode selection module coupled to the ischemia detection module, wherein the electrode selection module compares the relative proximity of each of the electrodes to the cardiac ischemia or infarct region and is adapted to select an electrode from the multiple-electrode lead that is relatively less proximate the cardiac ischemic or infarct region than another electrode of the multiple-electrode lead.

2. The IMD of claim 1, wherein the ischemia detection module is operable to define the region as being proximate one or more electrodes of the multiple-electrode lead.

3. The IMD of claim 1, wherein the ischemia detection module is operable to evaluate intracardiac electrogram (IEGM) data from an individual previously selected pacing electrode of the multiple-electrode lead and upon detection of the cardiac ischemia or infarct to evaluate IEGM data from each electrode of the multiple-electrode lead.

4. The IMD of claim 1, wherein the electrode selection module is operable to map the region based upon an extent to which individual electrodes are affected by the cardiac ischemia or infarct.

5. An implantable medical device (IMD) comprising:
   a detection mechanism operable to detect cardiac ischemia or infarct in a patient's cardiac tissue, wherein the mechanism to detect cardiac ischemia or infarct is operable to evaluate intracardiac electrogram (IEGM) data from each electrode on a multiple-electrode lead to detect the relative proximity of the cardiac ischemia or infarct region from each electrode of the multiple electrode lead; and,
   a selection mechanism coupled to the detection mechanism, the selection mechanism being operable to select an electrode for cardiac pacing based on the relative proximity of that electrode to the cardiac ischemic or infarct region as detected by the detection.

6. The IMD of claim 5, wherein the mechanism operable to detect is further operable to detect the cardiac ischemia or infarct from one or more contractility sensors positioned proximate the electrode and another electrode.

7. The IMD of claim 5, wherein the electrode and the another electrode comprise a subset of electrodes on a lead that are available for pacing and wherein the mechanism operable to detect is operable to evaluate IEGM data from each electrode of the lead and wherein the mechanism operable to select is operable to select the electrode on the lead that is least affected by the cardiac ischemia or infarct.

8. The IMD of claim 5, wherein the mechanism operable to select is operable to establish all electrodes that are available for a given pacing therapy and to compare the effect of the cardiac ischemia or infarct upon each of the available electrodes.

9. The IMD of claim 5, wherein the mechanism operable to select is operable to establish all electrodes that are available for a given pacing therapy and to compare the effect of the cardiac ischemia or infarct for each of the available electrodes and to select a pair of pacing electrodes that includes the electrode and wherein a pathway extending between the pair of pacing electrodes does not pass through tissue affected by the cardiac ischemia or infarct.

10. In an implantable medical device, a method comprising:
    sensing intracardiac electrogram (IEGM) data from each electrode of a multiple-electrode lead;
    evaluating the IEGM data to detect a cardiac ischemic region or infarct in proximity of each the electrode; and
    interpreting contractility data gathered proximate the electrode for indications of diminished contractility;
    determining the relative proximity of each electrode of a multiple-electrode lead to a region of cardiac ischemia or infarct as a function of the detected ischemic regions and the contractility data; and
    pacing through a different electrode of the multiple-electrode lead in an instance where a selected electrode is determined to be more proximate the region than other non-selected electrodes of the multiple-electrode lead.

11. The method as recited in claim 10, wherein the determining comprises: sensing intracardiac electrogram (IEGM) data from individual electrodes of the multiple-electrode lead and evaluating the sensed IEGM data from the individual electrodes to detect the cardiac ischemia or infarct; and, ranking the individual electrodes based upon relative proximity to the cardiac ischemia or infarct according to an extent that the cardiac ischemia or infarct was detected in the respective IEGM data.

12. The method as recited in claim 11, further comprising selecting the different electrode of the individual electrodes that is least proximate to the cardiac ischemia or infarct.

* * * * *